(12) United States Patent
Ott et al.

(10) Patent No.: US 6,447,520 B1
(45) Date of Patent: Sep. 10, 2002

(54) IOL INSERTION APPARATUS WITH IOL ENGAGEMENT STRUCTURE AND METHOD FOR USING SAME

(75) Inventors: Robert D. Ott, Irvine; Robert E. Glick, Lake Forest; Daniel G. Brady, San Juan Capistrano, all of CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/812,054

(22) Filed: Mar. 19, 2001

(51) Int. Cl.7 .................................................. A61F 9/00
(52) U.S. Cl. ...................................................... 606/107
(58) Field of Search ................................ 606/107, 161, 606/167; 623/6.12, 907, 6.63, 4.11; 604/220, 293, 294

(56) References Cited

U.S. PATENT DOCUMENTS

| | | |
|---|---|---|
| 4,681,102 A | 7/1987 | Barell |
| 5,643,276 A | 7/1997 | Zaleski |
| 5,702,402 A | 12/1997 | Brady |
| 5,800,442 A | 9/1998 | Wolf et al. |
| 5,947,975 A * | 9/1999 | Kikuchi et al. ............. 606/107 |
| 6,010,510 A | 1/2000 | Brown et al. |
| 6,241,737 B1 * | 6/2001 | Feingold .................... 606/107 |
| 6,248,111 B1 * | 6/2001 | Glick et al. ................. 606/107 |
| 6,251,114 B1 * | 6/2001 | Farmer et al. ............... 606/107 |
| 6,254,607 B1 * | 7/2001 | Makker et al. .............. 606/107 |
| 6,283,975 B1 * | 9/2001 | Glck et al. .................. 606/107 |

OTHER PUBLICATIONS

Brochure: Sensar™ Acrylic IOL, "Get the Clear Advantage of Sensar™." Copyright 2000.
Brochure: Sensar™ Acrylic IOL, "Instructions for Use—The Unfolder200 Sapphire Series With Sensar™ IOLs." Copyright 2000.

* cited by examiner

*Primary Examiner*—Pedro Philogene
(74) *Attorney, Agent, or Firm*—Stout, Uxa, Buyan & Mullins, LLP; Frank J. Uxa; Peter Jon Gluck

(57) ABSTRACT

An IOL insertion apparatus including a cartridge with an IOL-receiving chamber, a handpiece into which the cartridge is loaded, and a plunger rod that extends through a lumen in the cartridge to reliably engage the IOL therein. The chamber has a recess in one wall that creates a space adjacent the proximal edge of the IOL positioned therein. A lip or projection on the plunger rod is aligned with the space to extend underneath the proximal edge of the IOL. The plunger rod may define a forked end with a groove into which the proximal edge of the IOL is captured. The cartridge may be of the type that folds the IOL therein. The recess may continue the entire length of the cartridge to guide the plunger rod therethrough. The cartridge lumen may converge so that the IOL is further compressed therealong. An inwardly-directed wall portion in the cartridge may help guide the lip of the plunger rod into the recess.

30 Claims, 7 Drawing Sheets

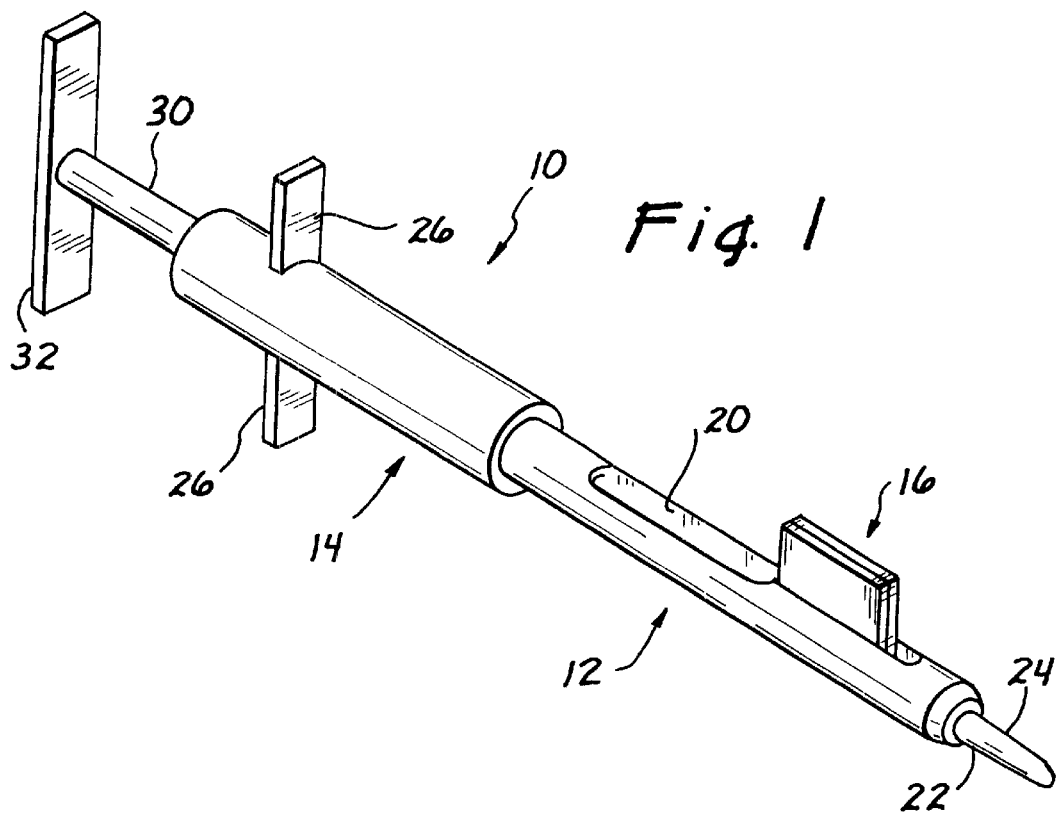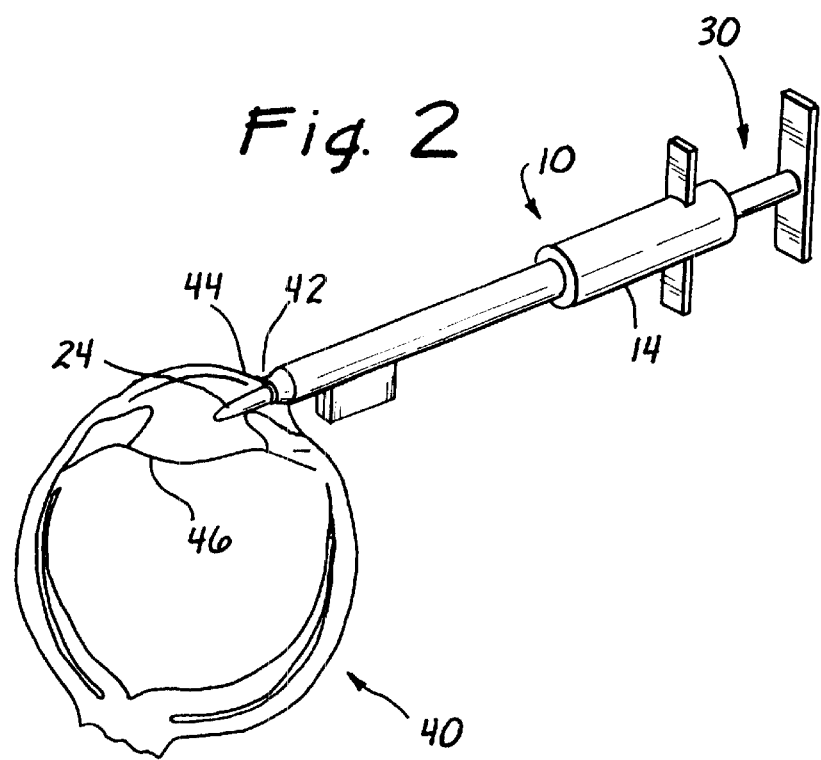

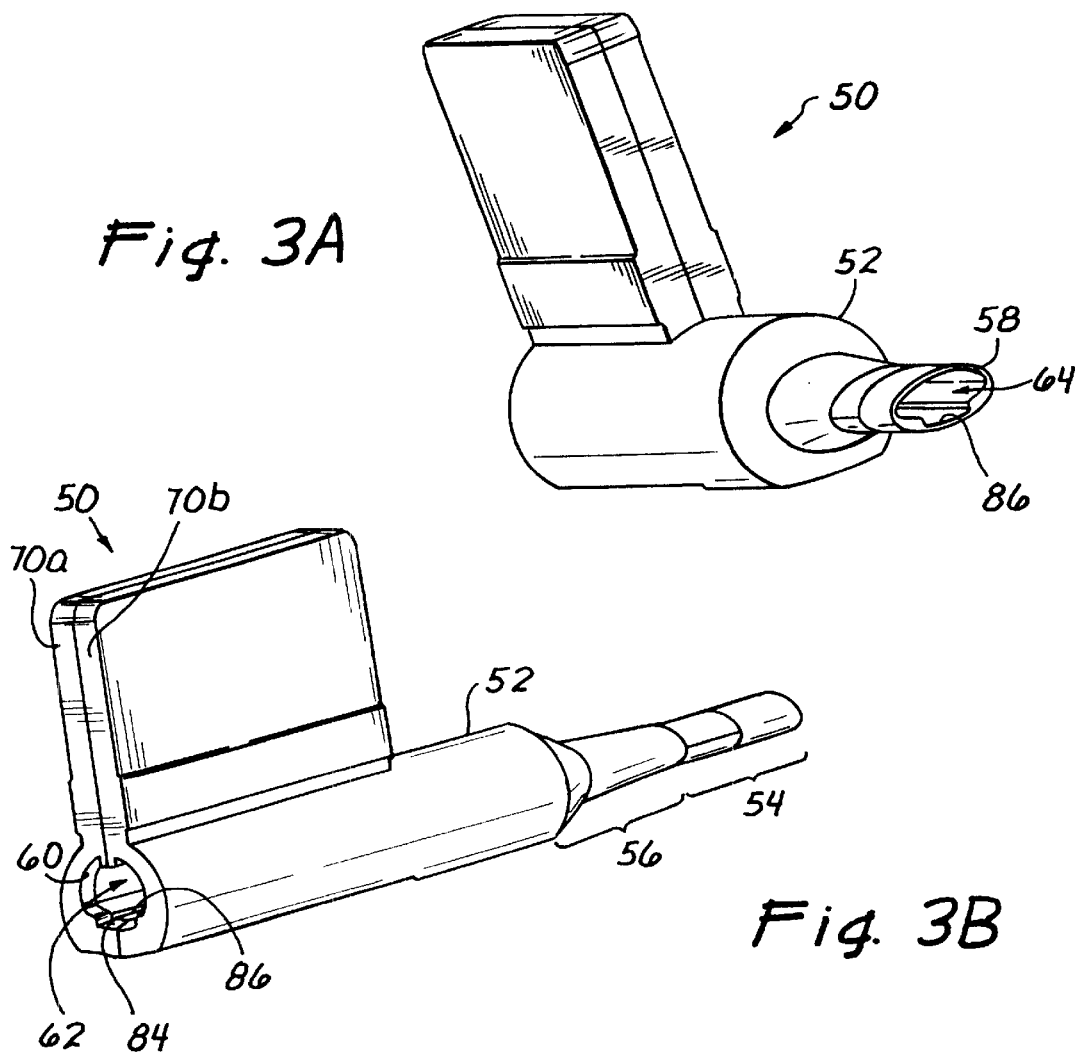
Fig. 3A
Fig. 3B
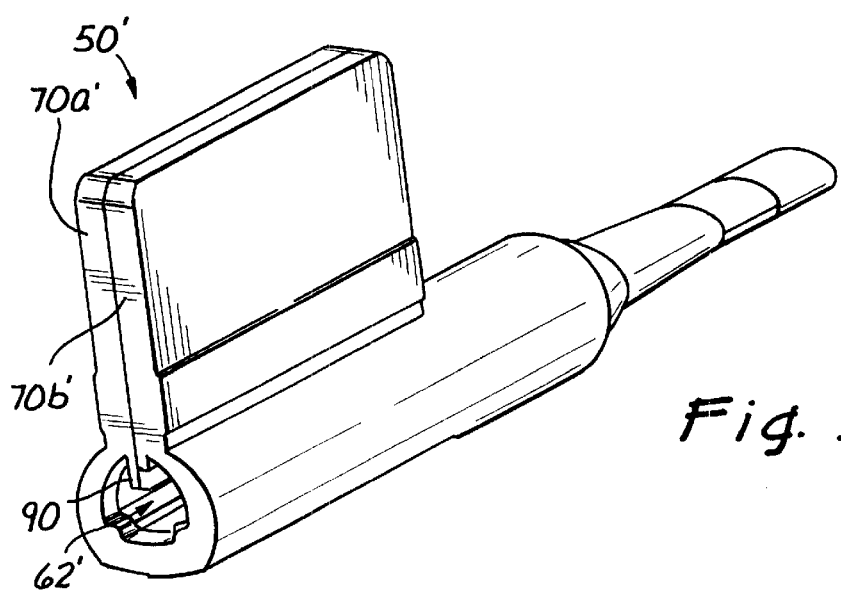
Fig. 3C

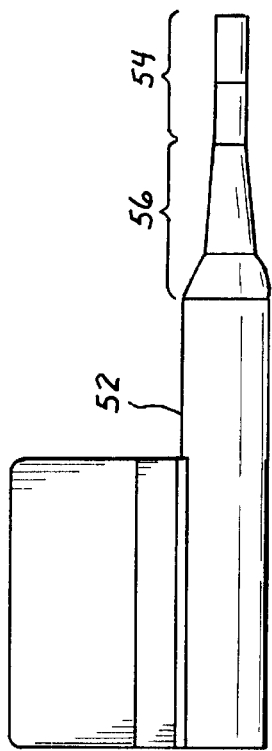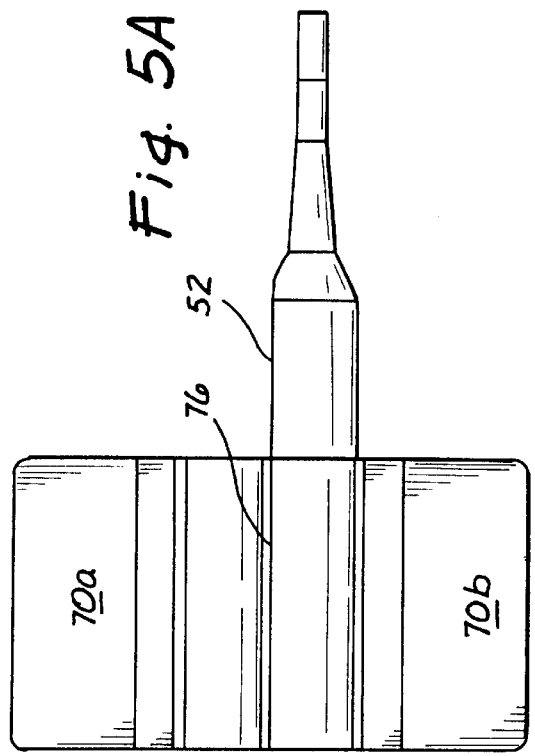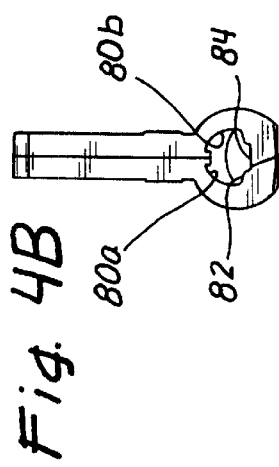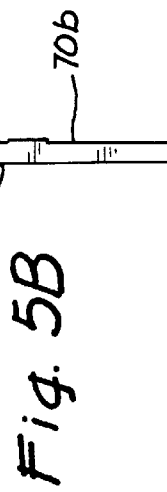

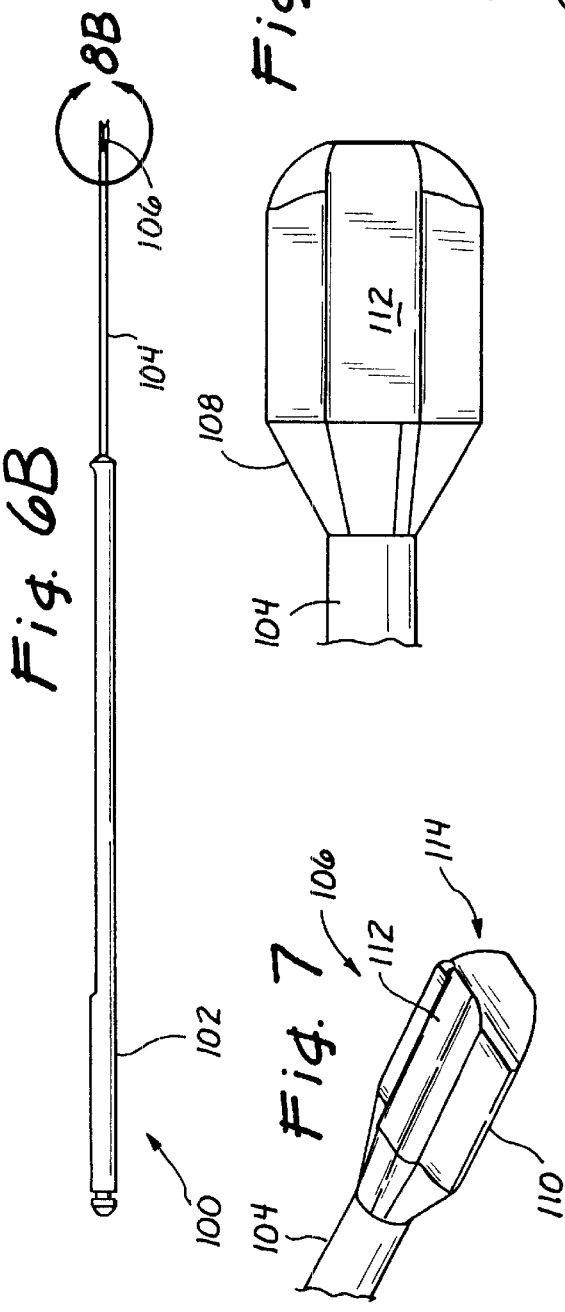

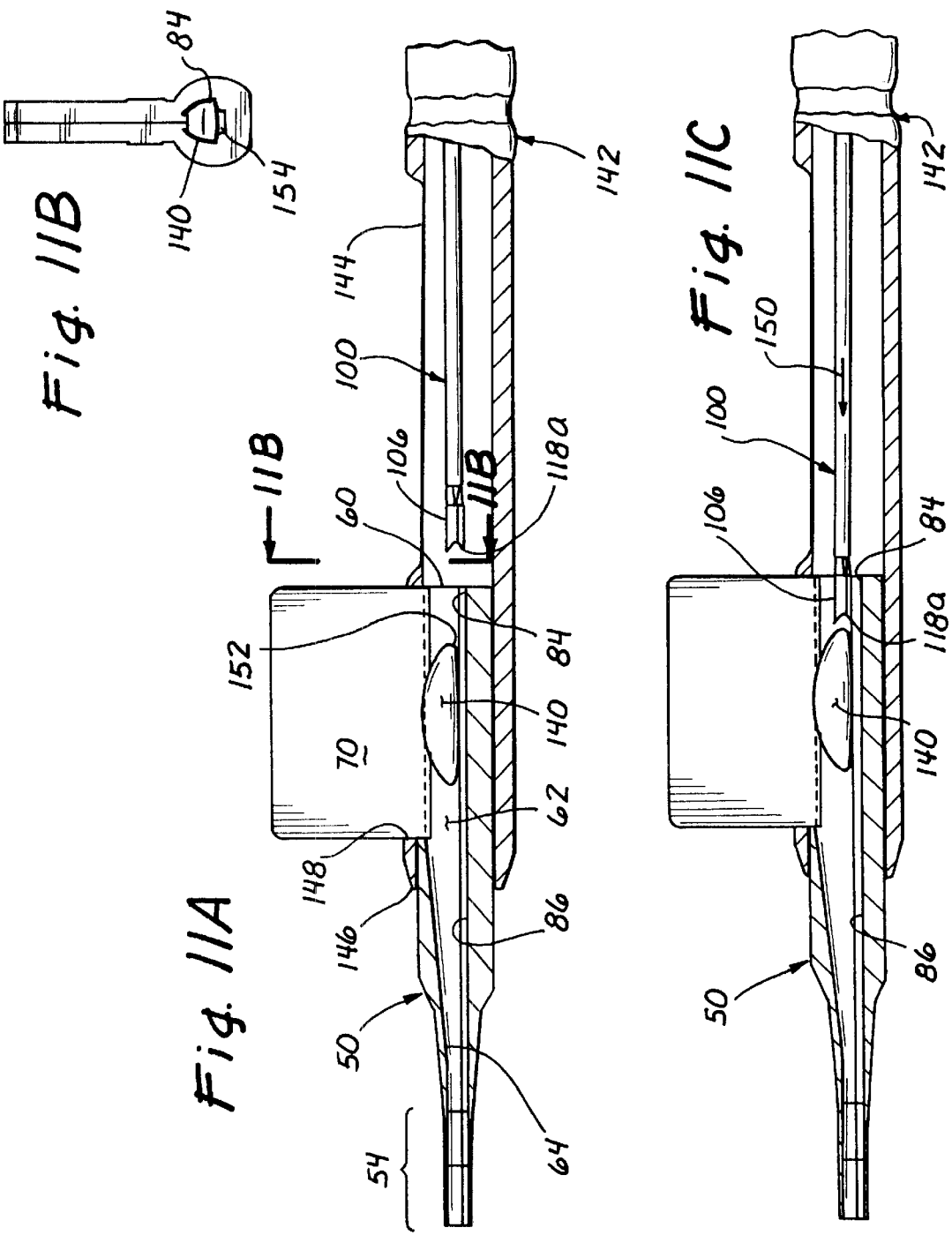

IOL INSERTION APPARATUS WITH IOL ENGAGEMENT STRUCTURE AND METHOD FOR USING SAME

BACKGROUND OF THE INVENTION

The present invention relates to apparatus and methods for inserting an intraocular lens through a small incision into an eye. More particularly, the invention relates to such apparatus and methods utilizing a plunger to displace an intraocular lens through a tubular insertion apparatus, wherein the intraocular lens is reliably and safely engaged by the plunger.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic, which extends from the optic and becomes affixed in the eye to secure the lens in position. The optic normally includes an optically clear lens. Implantation of such IOLs into the eye often involves making an incision in the eye. Making the incision as small as possible reduces trauma and speeds healing.

IOLs are known which are foldable (deformable) so that the IOL can be inserted into the eye through an incision smaller than the diameter of the lens.

Some of the most generally accepted insertion apparatus employ a hollow insertion tube having a diameter which permits the folded IOL to pass freely through the tube without permanent deformation, and without causing the surgeon to apply excessive force to overcome friction between the walls of the insertion tube and the IOL. Excessive force can result in the premature ejection of the IOL before the surgeon is ready to position it within the patient's eye. It would be advantageous to provide IOL insertion apparatus and methods which facilitate the passage of a folded IOL through the apparatus and the insertion of the IOL in the eye in easy, effective and controlled manner while avoiding damage to the IOL and undue trauma to the patient.

A very useful technique for inserting an IOL into the eye includes the use of an IOL injector or cartridge, such as the IOL injector described in Bartell, U.S. Pat. No. 4,681,102, and also in Brady, U.S. Pat. No. 5,702,402. These IOL injectors include a load chamber which is connected to an injection tube. The load chamber includes a lumen for receiving the IOL and is hinged so that the side walls thereof can be opened like a book. Closure of this lumen folds the IOL and maintains the IOL in a folded state. The injection tube includes a small diameter distal tip which is insertable into the incision within the eye. The cartridge is held in a handpiece which is coupled to a plunger rod. The plunger rod moves distally through the load chamber and injection tube to urge the IOL to pass through the tube and into the eye. The IOL is thus transferred from the load chamber through the injection tube and into the eye. As the IOL moves from the load chamber distally though the injection tube, its folded configuration is further compressed by a narrowing of the injection lumen. These IOL injectors simplify the placement of the IOL within the eye and reduce chances of surgeon error.

Although the IOL can pass freely through the injection tube, it must first be secured by the engaging end of the plunger rod. Because the plunger rod extends fully through the cartridge, its engaging end must be sized small enough to pass through the narrowest lumen of the cartridge, at the distal end of the injection tube. At the same time, the load chamber is relatively larger than the injection lumen so that the surgeon can easily place the IOL therein for folding. Therefore, there is a relatively large space surrounding the plunger rod engaging end as it enters the load chamber. Additionally, most plunger rods are not rigidly guided along an axis, but are relatively loosely coupled to a drive mechanism so that there is some radial play at the engaging end. Moreover, the IOL and cartridge are made of materials that interact to produce a coefficient of friction therebetween that must be overcome when urging the IOL through the tube, even with the introduction of a lubricating medium. The loose fit of the plunger rod in the load chamber in conjunction with the friction between the IOL and cartridge often causes the plunger rod to fail to engage the proximal edge of the IOL. That is, unless the plunger rod squarely contacts the proximal edge of the IOL, it may miss completely or deform the edge and ride up over the IOL, with the end result that the IOL remains in place while the plunger rod passes therethrough.

An intraocular lens insertion apparatus that attempts to address this problem is disclosed in Brown, et al., U.S. Pat. No. 6,010,510, and includes an injector plunger having a blunt, rounded tip offset from the centerline of the plunger rod. The offset tip assures that the tip is biased downward against the bottom of the cartridge bore to help ensure proper engagement of the intraocular lens therein. However, there is still a possibility that the plunger tip might ride underneath or otherwise fail to engage the intraocular lens.

There is thus a need for a more effective and safe means for engaging and displacing an intraocular lens from within an insertion apparatus.

SUMMARY OF THE INVENTION

The present invention provides an improved apparatus for inserting an intraocular lens through an incision into an eye. The apparatus operates in an environment that is similar to existing systems, with a cartridge being loaded into a handpiece, and plunger rod of the handpiece extending through a lumen in the cartridge to push an intraocular lens from an injection tube of the cartridge through an incision in the eye. The apparatus of the present invention provides structure within the cartridge and on the plunger rod that ensures positive engagement between the plunger rod and the intraocular lens to more reliably advance the intraocular lens into the eye in the desired orientation.

In one particular embodiment, the present invention provides an intraocular lens insertion apparatus including a cartridge having a longitudinal lumen extending through an injection tube and terminating in a mouth on a distal end thereof. An intraocular lens chamber sized to contain an intraocular lens is defined on a proximal end of the cartridge and forms part of the lumen. The intraocular lens has a proximal edge and a distal edge with respect to the cartridge, and at least a portion of the chamber is configured with a non-circular cross-section such that, with the intraocular lens positioned therein, a space along one wall is created adjacent to the proximal edge of the lens. The apparatus further includes a housing adapted to hold the cartridge and having a lumen generally aligned with the cartridge lumen. A plunger rod having an engaging head is provided that can be linearly displaced along the housing lumen into the cartridge lumen with a distal lip of the engaging head aligned with the space. Displacement of the plunger rod in a distal direction causes the distal lip to enter the space adjacent the proximal edge of the intraocular lens such that the engaging head reliably engages the intraocular lens. In a preferred embodiment, the chamber opens at a hinge so that the intraocular lens can be folded therein. Also, the engaging head of the plunger rod may have a forked end defined by the distal lip and another lip spaced therefrom, with a groove formed therebetween for capturing the proximal edge of the intraocular lens. The space may be created by a recess in one wall of the cartridge, the recess being formed only at the proximal end of the cartridge or extending longitudinally in a channel. Alternatively, a raised area in one wall of the cartridge is provided with the proximal edge of the lens being elevated above the wall to create the space.

In another aspect of the invention, an intraocular lens insertion apparatus comprises a cartridge for receiving an intraocular lens in a proximal chamber. The cartridge defines a distal injection tube having a lumen in communication with the chamber along a common axis. The chamber further includes a generally tubular wall and being configured such that, with the intraocular lens positioned therein, a space along the wall is created adjacent to a proximal edge of the lens. The apparatus also includes a handpiece for mounting the cartridge and having a plunger rod adapted to be displaced generally along the axis. The plunger rod includes a bifurcated distal end with a pair of lips separated by a groove and sized to receive a proximal edge of the intraocular lens. One lip of the plunger rod aligns with the space such that displacement of the plunger rod reliably captures the proximal edge of an intraocular lens within the groove. The space may be created by a recess in the wall of the cartridge, the recess being formed only at the proximal end of the cartridge or extending longitudinally in a channel. Alternatively, a raised area in the wall of the cartridge is provided with the proximal edge of the lens being elevated above the wall to create the space. Desirably, the lumen converges from the chamber distally through the injection tube such that an intraocular lens is compressed in size upon passage therethrough. The plunger rod may define an engaging head on a distal end with a flattened oval-shaped body and an axially-extending projection on one wide side that terminates in the lip aligned with the space. Optionally, the cartridge may include an axially extending wall portion projecting inwardly to the chamber opposite the wall to help guide the distal end of the plunger rod such that the one lip extends into the space.

Another aspect of the invention is a method of inserting an intraocular lens into an eye including providing a cartridge, a housing, and plunger rod. The cartridge has a chamber for receiving an intraocular lens and a delivery lumen defining an axis and extending distally therefrom through an insertion tube. The cartridge mounts in the housing, and the plunger rod axially slides within housing and completely through the cartridge. The plunger rod has an engaging head on its distal end with an axially extending lip. The method includes placing an intraocular lens within the cartridge, the chamber being configured such that a space is created adjacent a proximal edge of an intraocular lens positioned therein. The method further includes mounting the cartridge in the housing with the plunger rod retracted in a proximal direction, positioning the insertion tube within the eye, and axially advancing the plunger rod in a distal direction. First, the lip on the plunger rod enters the space prior to contact between the engaging head and the proximal edge of intraocular lens. Further advancement of the plunger rod causes the engaging head to contact the proximal edge of the intraocular lens. Full advancement of the plunger rod expels the intraocular lens from the delivery lumen into the eye. Desirably, the chamber opens at a hinge and the method includes placing an unfolded intraocular lens in the open chamber and folding the intraocular lens by closing the chamber. Also, the chamber may be larger than the delivery lumen such that intraocular lens is compressed in size upon passage from the chamber to the delivery lumen. Finally, the cartridge may include an axially-extending wall portion directed into the chamber, wherein the method includes guiding the lip into the space upon contact of the distal end of the plunger rod with the wall portion.

In another method, an intraocular lens is positioned within a cartridge chamber such that a proximal edge of the lens extends beyond a proximal end of the cartridge. A plunger rod having a bifurcated engagement head is distally advanced such that the proximal edge of the lens is captured in a groove of the engagement head prior to entry of the plunger rod into the cartridge chamber. The captured lens is then urged through the chamber and from the injection tube into a patient's eye.

These and other aspects of the present invention will become apparent in the following detailed description and claims, particularly when considered in conjunction with the accompanying drawings in which like parts bear like reference numerals.

BRIEF DESCRIPTIONS OF THE DRAWINGS

FIG. 1 is a perspective view of a general insertion apparatus of the present invention;

FIG. 2 is a schematic perspective drawing showing the placement of an insertion tube of the insertion apparatus of FIG. 1 in the eye;

FIG. 3A is a frontal perspective view of a foldable cartridge of the present invention;

FIGS. 3C and 3B are rear perspective views of foldable cartridges of the present invention;

FIGS. 4A and 4B are side and rear elevational views, respectively, of the foldable cartridge of FIG. 3B in its folded state;

FIGS. 5A and 5B are side and rear elevational views, respectively, of the foldable cartridge of FIG. 3B in its unfolded state;

FIGS. 6A and 6B are plan and elevational views, respectively, of a plunger rod of the present invention;

FIG. 7 is a perspective view of an IOL engaging portion of the plunger rod of FIG. 6;

FIGS. 8A–8C are several views of the IOL engaging portion of FIG. 7;

FIG. 11A is a longitudinal sectional view through an insertion apparatus of the present invention prior to engagement of an IOL within the foldable cartridge by the plunger rod;

FIG. 11B is a view taken a long line 11B—11B in FIG. 11A showing the rear end of the foldable cartridge with an IOL folded therein;

FIG. 11C is a longitudinal sectional view similar to FIG. 11A and showing engagement of a rear edge of the IOL by the plunger rod;

Figure 12A:
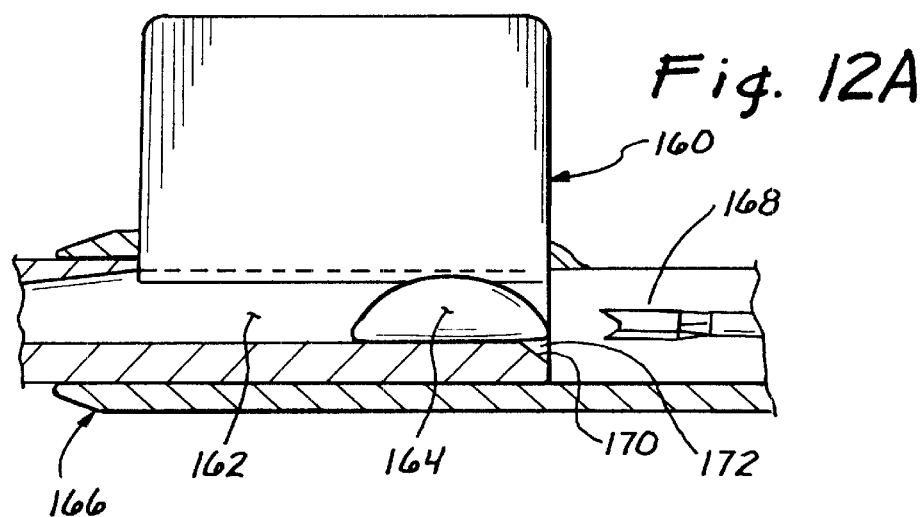
FIG. 12A is a longitudinal sectional view through an insertion apparatus showing an IOL positioned within an alternative foldable cartridge that creates a space below a proximal edge of the IOL to facilitate engagement by a plunger rod.
Figure 12B:
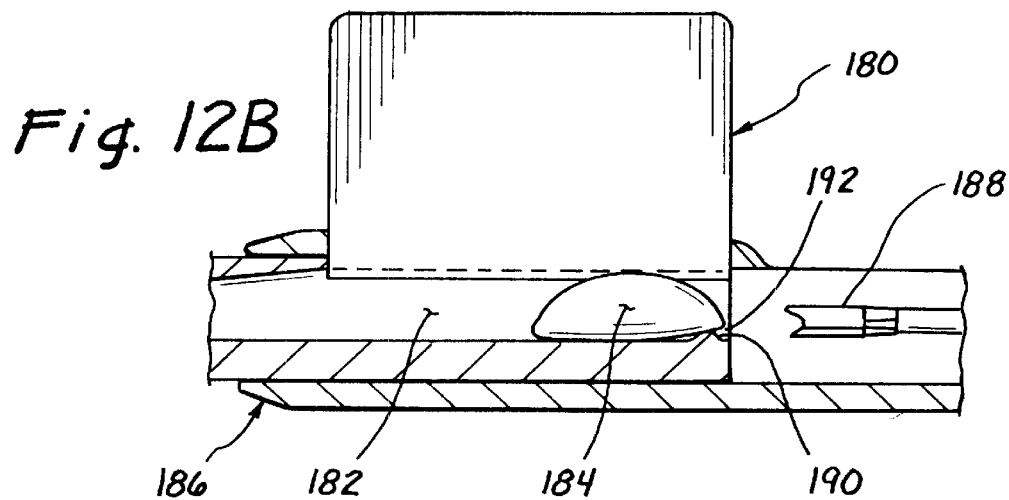
Figure 13:
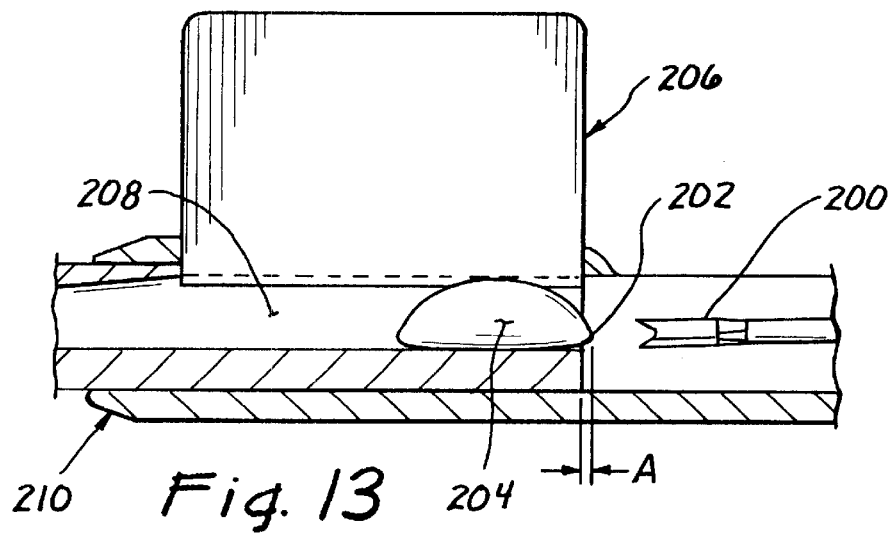

FIG. 12B is a longitudinal sectional view through an insertion apparatus showing an IOL positioned within a further alternative foldable cartridge that creates a space below a proximal edge of the IOL to facilitate engagement by a plunger rod; and FIG. 13 is a longitudinal sectional view through an insertion apparatus showing an IOL desirably positioned within a conventional foldable cartridge so that a proximal edge of the IOL extends beyond the cartridge to facilitate engagement by a plunger rod.

DETAILED DESCRIPTION OF THE PREFERRED EMBODIMENTS

FIG. 1 illustrates an IOL insertion apparatus, shown generally as 10, in accordance with the present invention. The apparatus 10 comprises a distal housing 12, a proximal housing 14 and a folding cartridge 16. Distal housing is operatively coupled to proximal housing 14. Distal housing 12 includes a through opening 20 through which the folding cartridge 16 can be placed. Distal housing 12 includes a forward opening 22 through which the injection tube 24 of folding cartridge 16 extends distally. Proximal housing 14 includes two oppositely disposed finger supports 26 which extend outwardly from the outer peripheral surface 28 of the proximal housing.

Apparatus 10 also includes a plunger rod 30 which includes an enlarged proximal end 32 effective to push plunger rod 30 through proximal housing 14, as will be discussed hereinafter.

Before proceeding to describe the operation of insertion apparatus 10, a brief description of the operation of folding cartridge 16 is provided. With reference to FIG. 2, the IOL is to be placed in the eye 40 into an area formerly occupied by the natural lens of the eye. With the IOL in its folded position within apparatus 10, as described below, injection tube 24 is ready for insertion through an incision 42 in the sclera 44 of eye 40. Capsular bag 46 protects the posterior segment of the eye 40 and as one of the eye's constituent parts which is not injured by the insertion of the IOL with the injection tube 24 inserted within the eye 40 and the distal end properly positioned, the surgeon advances plunger rod 30 by manually pushing the plunger rod 30 relative to proximal housing 14. This action moves IOL distally into injection tube 24. If needed, IOL can be repositioned in the eye by a small, bent needle or similar tool inserted into the same position.

FIG. 2 shows the sclera 44 having an incision through which the distal end portion of the injection tube 24 is passed. Alternately, the incision may be made through the cornea. Injection tube 24 preferably has a sufficiently small cross-section to pass into the eye 40 through an incision of about 3.5 mm or about 3.0 mm in the sclera 44. Once IOL is properly positioned in eye 40, and apparatus 10 is withdrawn from the eye, the incision in the sclera may be closed, for example, using conventional techniques. After use, folding cartridge 13, which is made of a polymeric material, such as polypropylene, preferably is disposed of. Remaining portions of apparatus 10, which preferably are made of metal, such as surgical grade stainless steel, may be reused after sterilization and disinfection. Any suitable material or materials of construction may be employed in the various components of the apparatus in accordance with the present invention.

With reference now to FIGS. 3–5, one specific embodiment of a foldable cartridge 50 of the present invention will be described. The foldable cartridge 50 may be used in the manner as described above for the folding cartridge 16 shown in FIGS. 1 and 2. The foldable cartridge 50 comprises a generally tubular body 52 defining an axis, with an injection tube 54 extending axially from a distal end thereof. The injection tube 54 is smaller in exterior dimension than the tubular body 52, and a convergence section 56 is provided therebetween. The distal end of the injection tube 54 defines a delivery mouth 58 on the distal end of the foldable cartridge 50, while the proximal end of the tubular body 52 defines an opening 60 leading to an IOL load chamber 62. The IOL load chamber 62 extends substantially the length of the tubular body 52, and continues in a delivery lumen 64 that gradually reduces in size through the convergence section 56 and terminates at the delivery mouth 58. A continuous axial chamber or lumen is thus defined through the foldable cartridge 50.

A portion of the tubular body 52 can be folded open as seen in FIGS. 5A and 5B. Specifically, a pair of planar wings 70a, 70b projecting radially from the tubular body 52 in its folded state, as seen in FIGS. 3–4, may be separated so that a half section 74a of the tubular body 52 opens from another half section 74b about an axially oriented hinge 76. Desirably, the foldable cartridge 50 is molded from a polymer such that the hinge 76 may be formed by a thin connecting portion (i.e., a living hinge) between the two half sections 74a, 74b. In the folded state of the cartridge 50, the interior walls of the two half sections 74a, 74b together define the IOL load chamber 62. In a preferred embodiment, one of the two half sections 74a, 74b is continuous and fixed with respect to the tubular body 52, while only the other of the half sections pivots about the hinge 76. This can be seen best in FIG. 5B.

With reference to the perspective views of FIG. 3B and the end elevation of view of FIG. 4B, the opening 60 has an irregular shape for receiving and folding IOL therein, defined by a pair of curvilinear sidewalls 80a, 80b and a bottom wall 82 opposite the radially extending wings 70a, 70b. The bottom wall 82 is interrupted by a centrally located recess 84. As seen in FIG. 3D, the recess 84 may continue as a longitudinal channel 86 throughout all or portion of the tubular body 52, and further may continue through the delivery lumen 64, as seen in FIG. 3A. The purpose of the recess 84 will be described below when use of the present invention is explained. It should be noted that the recess 84 creates a non-circular cross-section for the opening 60 into the load chamber 62. Specifically, the circular cross-section is interrupted by the outwardly-directed relief created by the recess 84.

FIG. 3C illustrates the alternatives foldable cartridge 50' that is in many ways identical to the foldable cartridge 50, and thus like elements will be given the same number with a prime (') designation. The foldable cartridge 50' differs from the earlier embodiment because it has an axially extending wall portion 90 projecting into the IOL load chamber 62' from one of the wings 70a', 70b'. The function of the wall portion 90 is to help guide a plunger rod passing through the foldable cartridge 50', as will become clearer from the usage description below.

FIGS. 6–8 illustrate one specific embodiment of a plunger rod 100 of the present invention to be used in conjunction with the foldable cartridge 50. The plunger rod 100 is a thin, elongate member having a proximal handle 102, a distal extension rod 104, and an IOL engaging head 106 on a distalmost end. As seen best in FIG. 7, the IOL engaging head 106 comprises a neck 108 diverging from the extension rod 104 to a generally flattened oval body 110 having a longitudinal projection 112 on one of the wide sides thereof.

As best seen in FIG. 8B, the head 106 defines a bifurcated end 114 wherein a groove 116 is formed between a pair of projecting lips 118a, 118b. The bifurcated end 114 thus has a generally forked configuration. One of the lips 118a defines the end of the projection 112.

Figure 9:
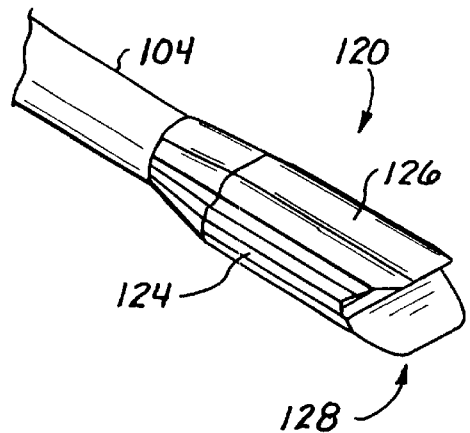
FIG. 9 is a perspective view of an alternative IOL engaging portion of a plunger rod of the present invention.
Figure 10C:
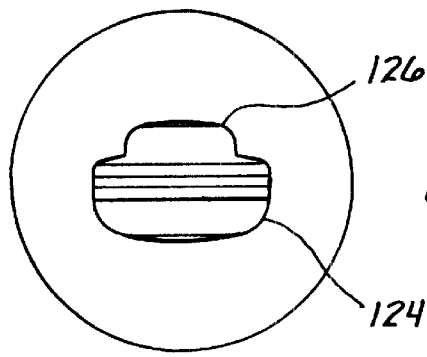
FIGS. 10A–10C are several views of the IOL engaging portion of FIG. 9.
Figure 10A:
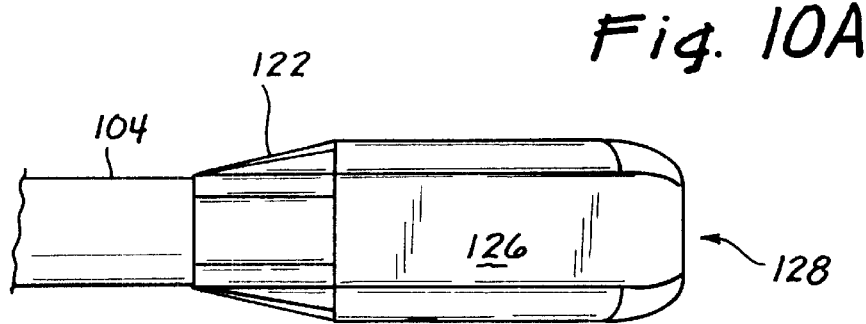

FIGS. 9–10 show an alternative IOL engaging head 120 that also exhibits a neck 122 diverging from the extension rod 104 and leading to a somewhat less flattened oval body 124 in comparison to the body 110 of FIGS. 6–8. As before, the body 124 exhibits a longitudinal projection 126, and terminates in a bifurcated (forked) end 128 defining a groove 130 between two lips 132a, 132b. The less flattened shape of the oval body 124 provides a little more clearance to the side of the body within the cartridge chamber to accommodate the fixation members or haptics of the IOL.

It should be noted that the bifurcated end of either of the IOL engaging heads described above can take a variety of forms. As illustrated, the depth of the groove between the two lips is approximately the same as, or slightly less than, the separation distance of the two lips. Of course, the depth of the groove can be more shallow, and can be other than the rounded V-shape as shown. The idea is to space the lips apart farther than the IOL edge thickness so that the edge can be captured within the groove. Further in this regard, the surfaces that contact the IOL are desirably rounded to prevent scoring or otherwise damaging the IOL.

Figure 10B:
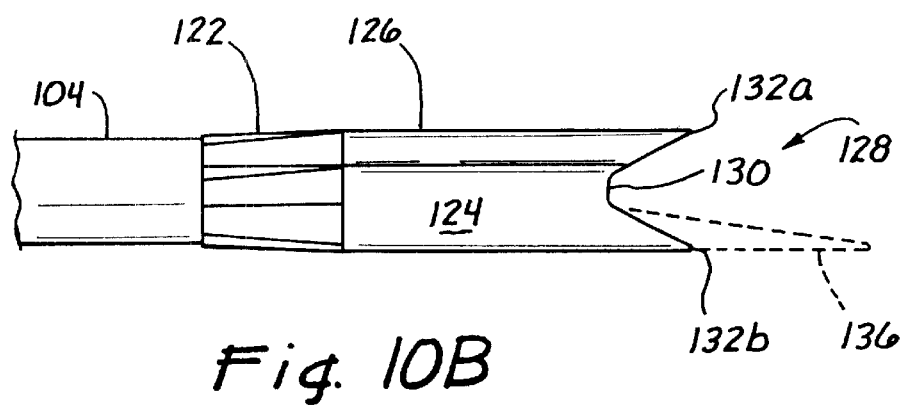

In a specific alternative to the plunger rods illustrated, the lower lip 118b, 132b of each can be extended axially beyond the upper lip 118a, 132a, as seen respectively at 134 in FIG. 8B and 136 in FIG. 10B. These extensions 134, 136 help ensure that the lower lip 118b, 132b travels underneath the IOL so that the IOL is captured in the rod grooves 116, 130. The extensions 134, 136 also serve as a sled of sorts during displacement of the IOL through the injection tube of the cartridge. The IOL and cartridge are made of materials that interact to produce a coefficient of friction therebetween that must be overcome when urging the IOL through the tube. As mentioned above, this frictional contact is a factor in causing the plunger rod to fail to engage the proximal edge of the IOL. By interposing the extensions 134, 136 under the IOL, the shared contact area between the IOL and cartridge is reduced, and the metal (e.g., stainless steel) of the extensions acts as a sled relative to the cartridge material to facilitate movement of the IOL through the cartridge.

In use, and with reference to FIGS. 11A–11C, an IOL 140 is placed within the cartridge 50 (or 50'). Preferably, the cartridge folds the IOL when the wings 70a, 70b are brought together, but the present invention is not limited to cartridges that deliver IOLs in folded configurations. That is, the reader will understand that the solution described herein to more reliably and safely engage an IOL with a plunger rod is equally applicable to non-folding embodiments.

With reference to the illustrate folding embodiment, the IOL 140 is placed within the half sections 74a, 74b with the wings 70a, 70b separated as seen in FIGS. 5A–5B. Upon bringing the wings 70a, 70b together, the half sections 74a, 74b come together to fold the IOL and define the IOL load chamber 62, as seen from the end in FIG. 11B. With the IOL 140 thus properly positioned within the foldable cartridge 50, the cartridge is positioned within a handpiece 142. The cartridge 50 is inserted through a longitudinal slot or opening 144 in the handpiece 142, and advanced distally until at least the injection tube 54 projects from a distal end 146 of the handpiece. In particular, the opening 144 aligns with a longitudinal slot (not numbered) ending at a stop surface 148 that contacts one of the wings 70 to prevent further advancement of the cartridge 50.

Once the cartridge 50 is properly positioned within handpiece 142, the plunger rod 100 (or 120) is axially advanced to the position shown in FIG. 11A. The plunger rod 100 is generally aligned with the proximal opening 60 of the cartridge 50, and the lower lip 118a of the IOL engaging head 106 aligns with the recess 84.

Further advancement of the plunger rod 100, as indicated by the arrow 150 in FIG. 11C, causes the IOL engaging head 106 to capture a proximal edge 152 of the IOL 140. That is, the bifurcated or forked configuration of the IOL engaging head 16 captures the proximal edge 152 in its groove 116 (FIG. 8B). To ensure reliable capture of the IOL 140 by the plunger rod 100, the lower lip 118a slides through the recess 84 so as to always pass underneath the proximal edge 152 of the IOL 140.

As seen in FIG. 11B, the recess 84 creates a space 154 underneath the IOL 140 into which the lower lip 118a extends. In this regard, the present invention is most suitable for use with IOLs that can be folded within the cartridge load chamber 62 without substantially deforming into the recess 84, so as to ensure a sufficient space 154 into which the lip 118a fits. As mentioned above, the separation distance between the lower lip 118a and the upper lip 118b is sufficient to always surround the proximal edge 152. In this manner, the proximal edge 152 is guided into the groove 116, thus capturing the IOL by the plunger rod 100. Subsequently, the IOL 140 may be distally advanced through the cartridge 50 and out the delivery mouth 158 into the capsular bag of the eye.

As described above, the recess 84 may continue longitudinally in a channel 86 that extends the entire length of the cartridge 50. This is seen in the cross sections of FIGS. 11A and 11C. The channel 86 guides the projection 112 of the IOL engaging head 106 during passage through the cartridge 50. In addition, the converging cross-section of the lumen through the cartridge from the IOL load chamber 62 to the delivery lumen 64 can also be seen.

If the cartridge 50' incorporates the inwardly projecting wall portion 90, seen in FIG. 3C, the IOL engaging head 106 is constrained in relation to the IOL load chamber 62 such that the projection 112 remains within the channel 86. In particular, the distance between the innermost edge of the wall portion 90 and the bottom wall 82 (see FIG. 4B) of the IOL load chamber 62 is such that the wall portion may contact the IOL engaging head 106 and align the lip 118a with the recess. Stated another way, the wall portion 90 provides additional structure to ensure that the lower lip 118a passes into the space 154 (FIG. 11B) below the IOL 140. The relevant dimensions are such, however, that at least a small amount of clearance remains for uninhibited passage of the IOL engaging head 106 through the load chamber 62, and subsequently through the lumen 86. The wall portion 90 is desirably beveled on its leading edge so that any misalignment of the plunger rod 100 can be corrected prior to the IOL engaging head 106 reaching the IOL 140.

FIG. 12A illustrates an alternative foldable cartridge 160 in accordance with the present invention having a cartridge chamber 162 for receiving an intraocular lens 164. As before, the cartridge 160 is adapted to be inserted and secured within a handpiece 166 such that a plunger rod 168 is aligned with and can translate through the cartridge chamber 162. The plunger rod 168 may be as described above, with a bifurcated or "scooped" front end for engaging a proximal edge of the intraocular lens 164 and urging the lens through the cartridge 160.

A recessed region 170 is formed on the end of the cartridge chamber 162 facing the plunger rod 168 that creates a space 172 below the proximal edge of the intraocular lens 164. In the illustrated embodiment, the recessed region 170 comprises a linear chamfer, although other recessed configurations such as a curvilinear chamfer will work. The region 170 is recessed radially outward from one wall of the chamber 162, in this embodiment a "bottom wall" opposite the radially extending wings of the folding cartridge (described above). The bottom wall is typically tubular and contacts a main portion of the intraocular lens 164, such that the space 172 is defined radially outward of the bottom wall and renders the wall non-circular.

The intraocular lens 164 must be positioned within the cartridge 160 such that the proximal edge projects over the recessed region 170. Upon advancement of the plunger rod 168, the bifurcated end more reliably captures the proximal edge of the intraocular lens 164 because of the space 172. That is, the lower lip of the bifurcated end extends within the space 172 and under the proximal edge of the intraocular lens 164. This configuration ensures engagement of the plunger rod 168 with the intraocular lens 164.

FIG. 12B illustrates a further foldable cartridge 180 having a load chamber 182 for receiving an intraocular lens 184. Again, a handpiece 186 holds the cartridge 180 such that a plunger rod 188 is aligned with the chamber 182 for advancement of the intraocular lens 184. To facilitate engagement of the plunger rod 188 with the proximal edge of the intraocular lens 184, one side of the cartridge chamber 182 is provided with a ramp or raised area 190. The intraocular lens 184 is positioned such that the proximal edge lies on the raised area 190 and is lifted above the side wall of the chamber 182, and a space 192 is created therebelow. In this manner, the bifurcated end of the plunger rod 188 more reliably captures the proximal edge of the intraocular lens 184. The raised area 190 projects radially inward from one wall of the chamber 162 (i.e., the "bottom wall") and is desirably curved or otherwise ramped to prevent binding of the plunger rod 188. As before, the bottom wall is typically tubular and contacts a main portion of the intraocular lens 184, and the space 192 may be aligned with the bottom wall or may be defined radially outward of the bottom wall. The raised area 190 thus creates a non-circular cross-section for the load chamber 182.

FIG. 13 illustrates an advantageous arrangement of a conventional intraocular lens insertion system that facilitates engagement of a plunger rod 200 with a proximal edge 202 of an intraocular lens 204. As before, a foldable cartridge 206 having a chamber 208 for receiving the lens 204 inserts within a handpiece 210. The intraocular lens 204 is deliberately positioned within the cartridge 206 such that the proximal edge 202 extends beyond the cartridge in the direction toward the plunger rod 200. The extent of projection of the proximal edge 202 is shown as distance A, and is sufficient to promote engagement of the bifurcated end of the plunger rod 200 with the proximal edge. With this arrangement, a conventional intraocular lens insertion system can be adapted such that the plunger rod more reliably engages the lens.

The present invention provides a cartridge that is designed to produce a space or recess underneath the proximal edge of the IOL to facilitate engagement by the plunger rod. It should be understood, however, that a small space may exist underneath both the proximal and distal edges of the IOL in its folded configuration within a conventional circular cross-section load chamber. A majority of IOLs have a bi-convex optic that includes a generally planar, disk portion perpendicular to the optical axis, and oppositely directed convex portions projecting from the disk portion along the optical axis in the anterior and posterior directions. In its relaxed, unfolded state, with one of the convex portions placed on a flat surface, the surrounding edges are naturally elevated from that surface. When folded within a conventional load chamber, this edge elevation is reduced somewhat, but a small space may still exist, as indicated schematically by the curvature of the folded IOLs in the figures. This can be visualized by the informal characterization of the folded IOL as being the shape of a taco shell.

The height of the space at the proximal edge of the folded IOL produced by the normal convexity thereof may be up to 0.015 inches, typically between 0.003–0.015 inches. The various cartridge embodiments of the present invention increase this existent space to an extent that insures engagement by the plunger rod. For example, the space created under the IOL in the embodiment shown FIGS. 11A and 11C may be double the space created by the normal convexity of the IOL. Specifically, the space created under the proximal edge of the IOL by the present invention is increased to between 0.003–0.020 inches, and preferably between 0.005–0.015 inches. In contrast, an exemplary plunger rod includes a bifurcated engaging head having forwardly directed lips spaced apart by about 0.040 inches, the lips having rounded distal tips having a radius of about 0.002 inches.

While this invention has been described with respect of various specific examples and embodiments, it is to be understood that the invention is not limited thereto and that it can be variously practiced within the scope of the following claims.

What is claimed is:

1. An apparatus for inserting an intraocular lens through an incision into an eye, comprising:

a cartridge having a longitudinal lumen, the cartridge including an injection tube on a distal end with a mouth opening to the lumen, and an intraocular lens chamber on a proximal end sized to contain an intraocular lens and forming part of the lumen, the intraocular lens including a lens body having a proximal edge and a distal edge, the intraocular lens chamber being configured with at least a portion having an irregular cross-section such that, with the lens body positioned therein, a space along one wall is created adjacent to the proximal edge of the lens body;

a housing adapted to hold the cartridge and having a lumen generally aligned with the cartridge lumen; and a plunger rod adapted to be linearly displaced along the housing lumen and into the cartridge lumen, the plunger rod being generally aligned with the cartridge lumen and having an engaging head with a distal lip aligned with the space, wherein displacement of the plunger rod in a distal direction causes the distal lip to enter the space adjacent the proximal edge of the lens body such that the engaging head reliably engages the intraocular lens.

2. The apparatus of claim 1, wherein the chamber opens at a hinge so that the intraocular lens can be folded therein.

3. The apparatus of claim 1, wherein the longitudinal lumen converges from the chamber to the distal mouth such that the intraocular lens body is compressed in size upon passage therethrough.

4. The apparatus of claim 1, wherein the space is defined by a recess formed in the one wall, the recess continuing as a longitudinal channel through at least a portion of the longitudinal lumen.

5. The apparatus of claim 4, wherein the channel continues through the entire longitudinal lumen.

6. The apparatus of claim 4, wherein the cartridge further defines an axially extending wall portion that projects inwardly to the chamber opposite from the recess, and wherein the distance between the innermost edge of the wall portion and the one wall of the chamber is such that the wall portion may contact the engaging head and align the distal lip with the recess.

7. The apparatus of claim 1, wherein the space is defined by a recess formed in the one wall only at the proximal end of the cartridge.

8. The apparatus of claim 7, wherein the recess is a chamfer extending radially outward of the one wall.

9. The apparatus of claim 1, wherein a raised area extends inward from the one wall of the cartridge such that the proximal edge of the lens body positioned thereon is lifted above the one wall to define the space.

10. The apparatus of claim 1, wherein the engaging head of the plunger rod has a forked end defined by the distal lip and another lip spaced therefrom, with a groove formed therebetween for capturing the proximal edge of the lens body.

11. The apparatus of claim 10, wherein the engaging head has a flattened oval-shaped body, with an axially-extending projection on one wide side that terminates in the distal lip.

12. The apparatus of claim 10, wherein one of the lips extends axially farther than the other.

13. An apparatus for inserting an intraocular lens through an incision into an eye, comprising:
a cartridge for receiving an intraocular lens including a lens body in a proximal chamber, the cartridge including a distal injection tube having a lumen in communication with the chamber along a common axis, the chamber further including a generally tubular wall and being configured with at least a portion having an irregular cross-section such that, with the intraocular lens positioned therein, a space along the wall is created adjacent to a proximal edge of the lens body; and
a handpiece for mounting the cartridge, the handpiece including a plunger rod adapted to be displaced generally along the axis, the plunger rod including a bifurcated distal end having a pair of lips separated by a groove sized to receive the proximal edge of the lens body, wherein one lip of the plunger rod is aligned with the space adjacent to the proximal edge of the lens body positioned in the chamber such that displacement of the plunger rod reliably captures the proximal edge within the groove.

14. The apparatus of claim 13, wherein the chamber opens at a hinge so that the intraocular lens can be folded therein.

15. The apparatus of claim 13, wherein the lumen converges from the chamber through the injection tube such that the intraocular lens body is compressed in size upon passage therethrough.

16. The apparatus of claim 13, wherein the space is defined by a recess formed in the wall, the recess continuing as a longitudinal channel through at least a portion of the lumen.

17. The apparatus of claim 16, wherein the channel continues through the entire lumen.

18. The apparatus of claim 16, wherein the cartridge further defines an axially extending wall portion that projects inwardly to the chamber opposite from the generally tubular wall, and wherein the distance between the innermost edge of the wall portion and the wall of the chamber is such that the wall portion contacts or is in close proximity to the distal end of the plunger rod and may align the one lip with the space.

19. The apparatus of claim 13, wherein the space is defined by a recess formed in the wall only at the proximal end of the cartridge.

20. The apparatus of claim 19, wherein the recess is a chamfer extending radially outward of the wall.

21. The apparatus of claim 13, wherein a raised area extends inward from the wall of the cartridge such that the proximal edge of the lens body positioned thereon is lifted above the wall to define the space.

22. The apparatus of claim 13, wherein the plunger rod defines an engaging head on a distal end with a flattened oval-shaped body and an axially-extending projection on one wide side that terminates in said one lip.

23. The apparatus of claim 13, wherein the lip of the plunger rod that is aligned with the space extends axially farther than the other lip.

24. A method of inserting an intraocular lens into an eye, comprising:
providing a cartridge including a chamber for receiving an intraocular lens including a lens body and a delivery lumen defining an axis and extending distally therefrom through an insertion tube;
providing a housing for mounting the cartridge;
providing a plunger rod axially slidable within the housing and having a length sufficient to extend completely through the cartridge when mounted in the housing, the plunger rod having an engaging head on its distal end with an axially extending lip;
placing an intraocular lens including a lens body within the cartridge, the chamber being configured with at least apportion having an irregular cross-section such that a space is created adjacent a proximal edge of the lens body positioned therein;
mounting the cartridge with the lens body therein in the housing with the plunger rod retracted in a proximal direction;
positioning the insertion tube within an eye;
axially advancing the plunger rod in a distal direction such that the lip enters the space prior to contact between the engaging head and the proximal edge of the lens body;
further axially advancing the plunger rod such that the engaging head contacts the proximal edge of the lens body; and
fully axially advancing the plunger rod to expel the intraocular lens from the delivery lumen into the eye.

25. The method of claim 24, wherein the chamber opens at a hinge, and wherein the method comprises placing the intraocular lens in an unfolded condition in the open chamber and folding the intraocular lens by closing the chamber.

26. The method of claim 24, wherein the space is defined by a recess formed in one wall of the cartridge.

27. The method of claim 26, wherein the recess is defined by a chamfer formed in the wall only at the proximal end of the cartridge facing the plunger rod.

28. The method of claim 26, wherein the recess continues as a longitudinal channel through at least a portion of the lumen, and wherein the plunger rod is guided along the delivery lumen by the engagement of the lip within the channel.

29. The method of claim 28, wherein the cartridge further includes an axially-extending wall portion directed into the chamber opposite from the channel, wherein the method includes guiding the lip into the channel upon contact of the engaging head of the plunger rod with the wall portion.

30. A method of inserting an intraocular lens into an eye, comprising:

providing a cartridge including a chamber for receiving an intraocular lens and a delivery lumen defining an axis and extending distally therefrom through an insertion tube;

providing a housing for mounting the cartridge;

providing a plunger rod axially slidable within the housing and having a length sufficient to extend completely through the cartridge when mounted in the housing, the plunger rod having an engaging head on its distal end with bifurcated lips separated by a groove;

placing an intraocular lens including a lens body within the cartridge with a proximal edge of the lens body extending proximally out of the cartridge chamber;

mounting the cartridge with the lens body substantially therein in the housing with the plunger rod retracted in a proximal direction;

positioning the insertion tube within an eye;

axially advancing the plunger rod in a distal direction such that the bifurcated lips surround the proximal edge of the lens body and cause the proximal edge to enter and be captured by the groove prior to the plunger rod entering the chamber; and further axially advancing the plunger rod and captured lens into the chamber and thereafter expelling the intraocular lens from the delivery lumen into the eye.

* * * * *

UNITED STATES PATENT AND TRADEMARK OFFICE
CERTIFICATE OF CORRECTION

PATENT NO.    : 6,447,520 B1
DATED         : September 10, 2002
INVENTOR(S)   : Ott et al.

It is certified that error appears in the above-identified patent and that said Letters Patent is hereby corrected as shown below:

Column 6,
Line 29, "FIG. 3D" should read -- FIG. 3B --.

Column 12,
Line 31, "apportion" should read -- a portion --.

Signed and Sealed this

Third Day of June, 2003

JAMES E. ROGAN
*Director of the United States Patent and Trademark Office*